United States Patent
Murakami et al.

(10) Patent No.: US 6,825,395 B1
(45) Date of Patent: Nov. 30, 2004

(54) TRANSGENIC NON-HUMAN MAMMALS EXPRESSING THE HUMAN COMPLEMENT INHIBITOR (DAF/CD55)

(75) Inventors: Hiroshi Murakami, Tsukuba (JP); Tatsuya Fujimura, Tsukuba (JP); Yoichi Takahagi, Tsukuba (JP); Koji Toyomura, Tsukuba (JP); Tamotsu Shigehisa, Tsukuba (JP)

(73) Assignee: Nippon Meat Packers, Inc., Osaka (JP)

(*) Notice: Subject to any disclaimer, the term of this patent is extended or adjusted under 35 U.S.C. 154(b) by 0 days.

(21) Appl. No.: 09/462,740
(22) PCT Filed: Jun. 30, 1998
(86) PCT No.: PCT/JP98/02927
§ 371 (c)(1), (2), (4) Date: Apr. 5, 2000
(87) PCT Pub. No.: WO99/03336
PCT Pub. Date: Jan. 28, 1999

(30) Foreign Application Priority Data

Jul. 14, 1997 (JP) ............................................. 9/205235

(51) Int. Cl.⁷ ............................................ A01K 67/027
(52) U.S. Cl. ............................... 800/14; 800/17; 800/18
(58) Field of Search ................................ 800/8, 14, 17

(56) References Cited

U.S. PATENT DOCUMENTS 6,255,474 B1 * 7/2001 Toyomura et al. ......... 536/24.1

FOREIGN PATENT DOCUMENTS

| JP | WO 9700951 | * | 1/1997 | ........... C12N/15/12 |
| WO | WO 91/05855 | | 5/1991 | |
| WO | WO 9302188 A | | 2/1993 | |
| WO | WO 97/12035 | | 4/1997 | |

OTHER PUBLICATIONS

Artip et al, 1997, Cur. Opin. Cardiol., 12: 172–178.*
Kuipers et al, 1997, Transgenic Res., 6: 253–259.*
Rosengard et al, 1995, Transplantation, 59: 1325–1333.*
Rosengard, Ariella M. "Tissue Expression of Human Complement Inhibitor, Decay, Accelerating Factor, In Transgenic Pigs" Transplantation, vol. 59, No. 9, May 15, 1995 pp. 1325–1337, XP000564395.
Oldham E R., et al. "High–Level Tissue Specific Expression of Human CD59, MCP, and DAF Proteins from Genomic Clones in Transgenic Mice" Transplantation ProceedingS, vol. 28, No. 2 Apr. 1, 1996 pp. 693–XP000644540 ISSN: 0041–1345.

* cited by examiner

Primary Examiner—Peter Paras
(74) Attorney, Agent, or Firm—Sughrue Mion, PLLC

(57) ABSTRACT

This invention provides transgenic mammals other than man carrying the gene of the human complement inhibitor (DAF/CD55) and expressing the human complement inhibitor in their organs and tissues, particularly in their endothelial cells. This invention provides nonhuman transgenic mammals useful as laboratory animals in the medical and pharmacological fields and/or sources of organs, tissues, cells and the like for medical treatment of man.

5 Claims, 6 Drawing Sheets

(A) B H K Li Lu S T (B) B H K Li Lu S T (C) B H K Li Lu S T

K562

TRANSGENIC NON-HUMAN MAMMALS EXPRESSING THE HUMAN COMPLEMENT INHIBITOR (DAF/CD55)

This application is the national stage entry of PCT/JP98/02927 filed Jun. 30, 1998, claiming benefit of Japanese application 9/205235 filed Jul. 14, 1997.

TECHNICAL FIELD

This invention provides transgenic mammals. Particularly, the invention provides the nonhuman transgenic mammals carrying the human complement-inhibitor (hDAF/CD55) gene. More particularly, the invention provides domestic and laboratory animals carrying the hDAF gene.

BACKGROUND OF THE INVENTION

Recently, studies on animal-to-man organ transplantation (xenotransplantation) have been carried out mainly in European countries and the United States. Because of close relation to human beings, apes may be desirable donors, but the use of their organs may be infeasible because of the shortage of these animals and their high intelligence. However, domestic animals, particularly pigs, have advantages of their organ sizes and shapes similar to those of man, easy supply due to mass rearing and established basic technology. Consequently, organ transplantation from the pig to man has mainly been studied.

If a porcine organ is transplanted to man, it will immediately (within minutes) and severely be rejected (hyperacute rejection), resulting in loss of its functions.

These phenomena are thought to be caused by a series of reactions: (1) Human blood contains endogenous antibodies against porcine cells (termed natural antibodies). If a porcine organ is transplanted to man, such antibodies recognize the porcine organ and form antigen-antibody complexes. (2) The antigen-antibody complexes activate complement in human serum and trigger the complement cascade reaction. The attachment of C1 to the antigen-antibody complexes triggers reactions of C4 and C2. resulting in formation of C3 convertase, which activates C3 and cleaves it to C3b and C3a. The attachment of C3b to the cell surface of the porcine organ results in formation of C5 convertase, which activates C5 and cleaves it to C5b and C5a. The attachment of C5b to the cell surface results in sequential attachments of C6, C7, C8 and C9. (3) In consequence of the complement cascade reaction, the membrane attack complex (MAC) is formed (termed the classical complement pathway). MAC attaches the transplanted organ and causes thrombosis. (4) The alternative complement pathway is known to cause also the same cascade reaction as described above after the C3 step and finally to form MAC.

Miyagawa, S. et al. (Transplantation, Vol. 46(6), 825–830, 1988) reported the following: (1) the complement cascade reaction triggered hyperacute rejection of xenografts via the classical and/or alternative pathway; (2) no hyperacute rejection occurred, if the recipients had previously been treated with CVF (cobra venom factor) to cause deprivation of C3. From such findings, it has long been desired to generate transgenic animals expressing membrane-bound DAF and/or MCP, especially those homologous to recipient species, which can inhibit the cascade reaction at the C3 step.

It has been tried to generate transgenic pigs expressing a complement inhibitor hDAF (CD55) to decompose human C3 convertase in the porcine organs (Rosengard, A. M. et al., Transplantation, Vol. 59(9). 1325–1333, 1995: G. Byrne et al., Transplantation Proceedings, Vol. 28(2), 759, 1996).

However, it has never been explained whether these transgenic pigs completely suppresses hyperacute rejection. Therefore, questions like the following should be answered: 1) Do these transgenic pigs express sufficient amounts of hDAF in target organs? 2) Is it necessary to co-express some other complement inhibitors? 3) Isn't it necessary to express sugar-transferase gene in order to reduce the antigen (sugar-chain antigen), which Is expressed on the porcine cells and to which human natural antibodies bind? 4) Isn't it necessary to co-express the above-described gene and other genes encoding the thrombosis-preventing protein and the like? Thus, many problems are left unsolved to overcome the hyperacute rejection.

To solve these problems, it is urgent to generate pigs and/or other small-sized laboratory animals that can be handled more easily than pigs and to examine these animals from various viewpoints. Particularly, in order to carry out studies in this field and/or to develop clinical application, it is valuable to generate transgenic pigs and/or small-sized easy-to-handle laboratory animals, of which tissues and organs express hDAF of at least the same amounts as or larger amounts than those expressed in man.

Therefore, it has been tried to generate transgenic pigs expressing the human complement inhibitors as described above. Expression was examined by such methods as the following; (1) in vitro immunohistological examination, (2) ex vivo examination by allowing the transgenic pig tissues to contact directly with human blood, or (3) in vivo examination by transplanting the transgenic pig tissues to primates. It was confirmed that the tissues from the transgenic pigs survived and functioned longer than those from non-transgenic pigs in ex vivo and in vitro examinations.

However, it was not necessarily explained whether the amounts of the human complement inhibitors expressed in the transgenic pig tissues were at least equivalent to or larger than those expressed in man.

To generate transgenic pigs expressing the human complement inhibitors, the following have been reported as the promoter genes of transgenes: (1) the promoter genes from nonporcine sources (G. A. Langford et al., Transplant. Proc., 26, 1400, 1994; W. L. Fodor et al., Proc. Natl. Acad. Sci. USA., 91, 11153–11157, 1994; G. W. Byrne et al., Transplantation, 63, 149–155, 1997) and/or (2) the promoter genes relating to molecules distributed throughout the whole bodies of animals (e.g., beta-actin, H2K$^b$).

Transgenic mice expressing hDAF have also been generated (N. Cary et al., Transplant. Proc. Vol. 25(1), 400–401, 1993; D. Kagan et al., Transplant. Proc. Vol.26(3), 1242, 1994). The loci and amounts of hDAF expressed in these transgenic mice, however, varied from report to report. Strictly speaking, no transgenic mouse expressing the human complement inhibitor in the due organ to develop it (particularly, vascular endothelial cells) in an amount larger than that expressed in human organ has ever been generated.

To solve the above problems, the present inventors studied to generate transgenic animals, particularly those other than man, expressing complement inhibitor(s) in the due organs, tissues and cells, particularly the vascular endothelial cells, in which the complement inhibitors should essentially be expressed. The inventors succeeded in generating transgenic animals fulfilling the purposes with the promoter gene of the porcine complement inhibitor (pMCP) previously invented by the inventors (see Japanese Patent Application No. 142961/1997), by introducing the transgene designed to express the complement inhibitor(s) in the due organs, tissues and cells, particularly in the vascular endothelial cells, in which the complement inhibitors should essentially be expressed, into animals' fertilized eggs, by implanting the eggs in the uteri of recipient animals and by obtaining their youngs.

The examples described below show that the transgenic mice of this invention expressed hDAF in various organs, tissues, endothelial cells, erythrocytes, and central and peripheral nerves in amounts larger than those expressed in human cells. Furthermore, the expression of hDAF was confirmed in their erythrocytes and nerves of the transgenic pigs of the invention.

This invention was accomplished on the basis of such findings. The purpose of the invention was to provide transgenic animals useful in the medical and pharmacological fields.

DISCLOSURE OF THE INVENTION

This invention is related to nonhuman mammals carrying the human complement inhibitor (DAF/CD55) gene and expressing the inhibitor in their organs and tissues. Furthermore, the invention is related to transgenic mammals expressing the human complement inhibitor (DAF/CD55) in their vascular endothelial cells, particularly in those of all the organs and tissues.

It is favorable that the transgenic mammals of the invention are carrying the promoter gene of the porcine complement Inhibitor (pMCP) at an upstream locus of the human complement-inhibitor (DAF/CD55) gene.

The transgenic mammals of this invention are useful as domestic and laboratory animals.

Figure 4:
FIG. 4 shows the PCR profiles obtained by examining the transgenic and nontransgenic mammals with hDAFcDNA-specific primers.

Lanes (1) and (3) of FIG. 4 show the PCR profiles of the hDAFcDNA-possitive pig and mouse, respectively. Lanes (2) and (4) show those of the hDAFcDNA-negative littermate pig and mouse, respectively.

Figure 5:
Figure 5:
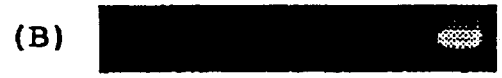
Figure 5:

FIG. 5 shows expression of mRNA of hDAF in various organs of a TgF1 mouse, a transgenic mouse generated for comparison and a normal mouse (nontransgenic mouse).

Figure 3:
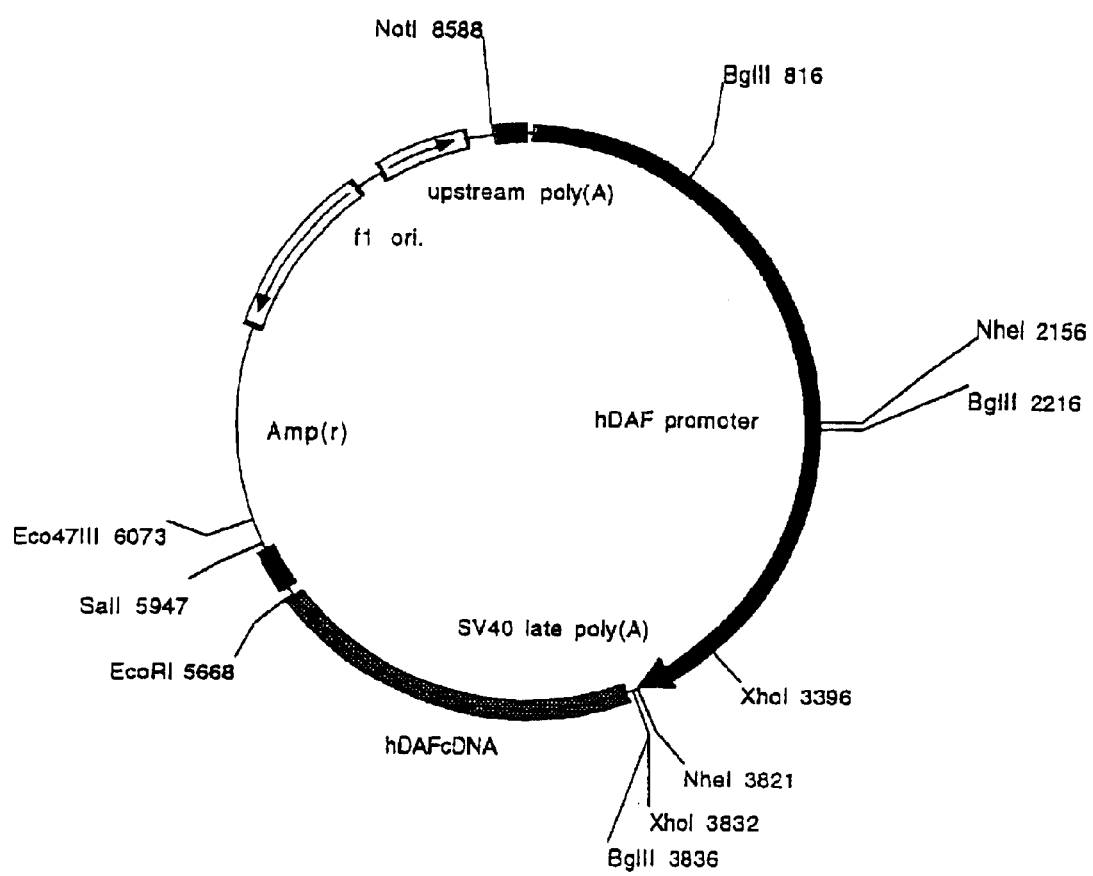
FIG. 3 illustrates the structure of the transgene comprising hDAF promoter and hDAFcDNA used for comparison.

Expression of mRNA in various organs of the TgF1 mouse is shown in FIG. 5(A); that of the transgenic mouse for comparison (generated by introducing transgene (3) comprising hDAF promoter and hDAFcDNA) (see FIG. 3) is shown in FIG. 5(B); that of the nontransgenic mouse is shown in FIG. 5(C) and that of human lymphocyte (K562) at the right end of FIG. 5(C). B, H, K, Li, Lu, S and T in each figure stand for the brain, heart, kidney, liver, lung, spleen and testis, respectively.

Figure 6A:
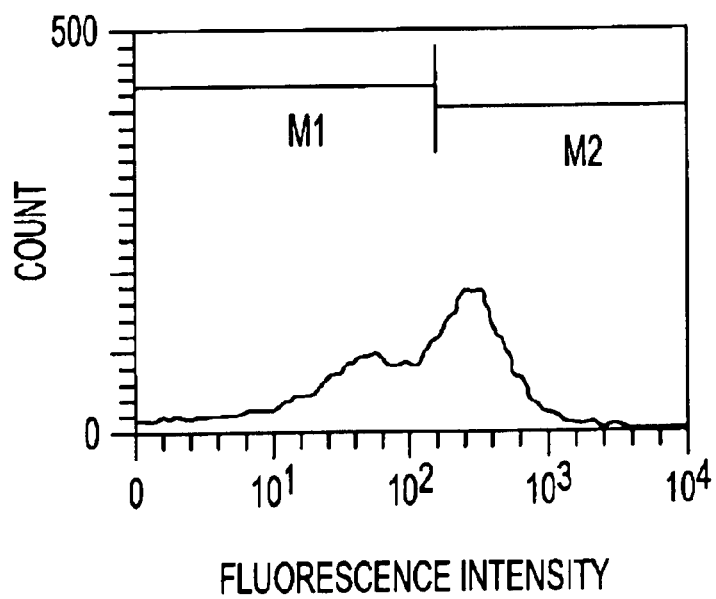
Figure 6B:
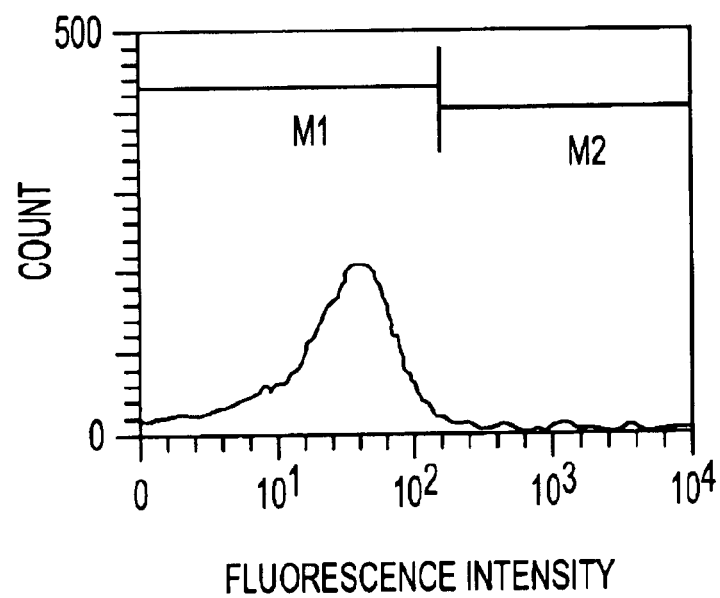

FIG. 6 shows FACS-analysis profiles obtained by treating erythrocytes from a transgenic pig and its nontransgenic littermale pig with anti-hDAF monoclonal antibodies. FIG. 6(A) shows that the erythrocytes from the transgenic pig expressed hDAF, whereas FIG. 6(B) shows that those from a nontransgenic littermate pig did not.

Figure 7:
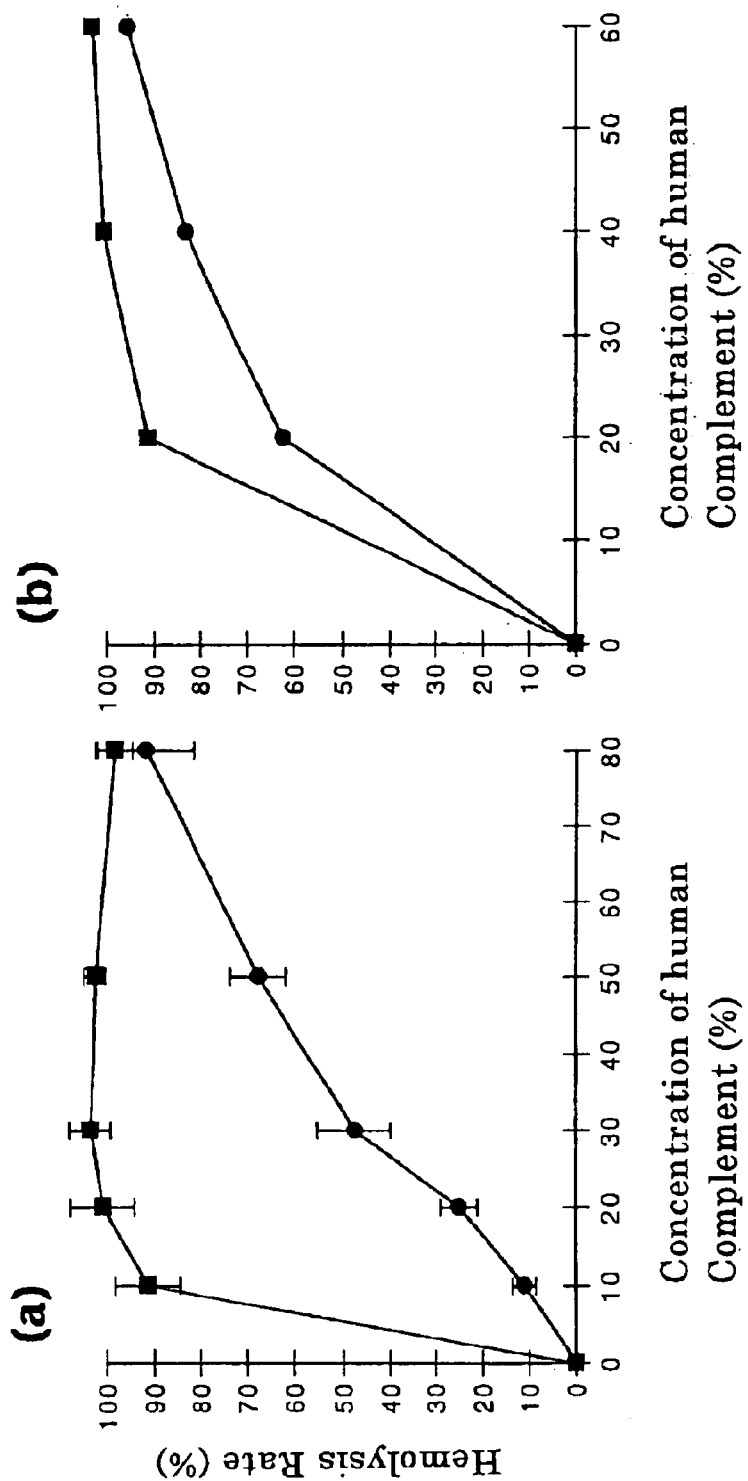

FIG. 7 shows hemolysis profiles obtained by treating erythrocytes from the transgenic (●) and normal (■) animals with human serum. Figures (a) and (b) show the hemolysis profiles of the mouse and porcine erythrocytes, respectively. The horizontal and the vertical axes of the figure represent the complement concentration in human serum and the degree of hemolysis, respectively.

THE BEST MODE FOR APPLYING THE INVENTION

As described above, the present invention provides non-human transgenic mammals carrying the human complement inhibitor (referred to as hDAF in the following) and expressing the inhibitor in their organs and tissues, particularly in the vascular endothelial cells. As far as it is other than man, the species of mammals of this invention is not restricted. Examples of mammals are the mouse, rat, hamster, pig, cattle, horse, sheep, rabbit, dog, cat and so on.

Transgenic mammals of the invention can be generated by the following methods:

First, transgene is prepared by binding promoter gene with hDAFcDNA. A part of an appropriate vector (e.g., pGL-3 basic vector, pBluescript and the like) is clipped out with a restriction enzyme(s), and the ends of the digested vector are truncated.

Base sequence encoding hDAF is clipped out from hDAFcDNA (see Medof, M. E. et al., Proc. Natl. Acad. Sci. USA., 84, 2007, 1987 for example) at an upstream locus of the initiation codon and at a downstream locus of the termination codon with a restriction enzyme(s), truncated and conventionally inserted into the above-described vector. An appropriate promoter gene is also inserted at an upstream locus of the hDAFcDNA-introduced locus.

Any promoter can be used, as far as it can induce expression of hDAF in the mammals' bodies. A promoter gene of endothelin is an example. The inventors found that a promoter gene of porcine complement inhibitor (PMCP) worked more efficiently. The base sequence of the promoter gene of pMCP is defined as Sequence No. 1 (see Japanese Patent Application No. 142961/1997).

From the vector thus prepared (circular gene), transgene is prepared by digesting the region including the promoter and hDAF genes with an appropriate restriction enzyme(s).

Methods to carry out the above-described processes are commonly known by those skilled in the art. The processes can conventionally be performed.

Transgenic mammals can be generated conventionally by introducing by microinjecting the above-described transgenes into mammals' fertilized eggs (those at the pronucleus phase), implanting the eggs in the oviducts of female mammals (recipient mammals) after a few additional incubation or directly in their uteri synchronized to the pseudopregnancy, and obtaining the youngs. If the pronuclei are hard to be recognized because of the presence of many fatty granules in the eggs, they may conventionally be centrifuged.

To find whether the generated youngs are transgenic, below-described dot-blotting, PCR, immunohistological, complement-inhibition analyses and the like can be used.

The transgenic mammals thus generated can be propagated by conventionally mating and obtaining the youngs, or transferring nuclei (nucleus transfer) of the transgenic mammal's somatic cells, which have been initialized or not, into fertilized eggs of which nuclei have previously been enucleated, implanting the eggs in the oviducts or uteri of the recipient mammals, and obtaining the clone youngs.

As shown in the below-described examples, it was confirmed that the transgenic mammals of this invention were carrying hDAF gene, expressing hDAF in the endothelial cells of all the organs and being resistant to the human complement.

INDUSTRIAL APPLICABILITY

The present invention is useful in the medical and pharmacological fields, exerting the following effects:

(1) If such organs as the heart, liver and kidney of the transgenic mammals of this invention are contacted with human blood or transplanted in primates, it can be confirmed that hDAF effectively prevents hyperacute rejection caused by xenotransplantation.

(2) If the xenotransplantion model is prepared by contacting such organs as the heart, liver and kidney of the transgenic mammals of this invention with human blood or transplanting the organs in primates, the model will help develop not only remedies, devices and the like to prevent hyperacute rejection after xenotransplantation but also those to prevent acute or chronic rejection after the hyperacute rejection.

(3) This invention makes it feasible to study hyperacute rejection-related problems hard to be solved only by expression of the complement inhibitors themselves. Namely, the invention may answer the questions whether it is necessary to introduce sugar transferases to reduce expression of sugar-chain antigens to which human natural antibodies bind, and/or to introduce factors to maintain homeostasis of the vascular endothelial cells (e.g., thrombomodulin. etc.).

(4) If the transgenic mammals of this invention are mated with those expressing some other complement inhibitor (human MCP or human CD59), synergic effects of the inhibitors can be examined.

(5) If the organs (e.g., the heart, lung, liver, kidney, pancreas, etc.), their adjunctive tissues (e.g., the coronary artery, endocranium, etc.) or cells (e.g., Langerhans islets producing insulin, nigrostriatal cells producing dopamine, etc.) from the transgenic mammals of this invention are transplanted to human patients whose organs have been damaged and their functions lost, they will supplement or substitute the functions of the patient organs.

(6) If the cells from the organs of the transgenic mammals of this invention (e.g., cells from the liver, kidney and the like, Langerhans islets producing insulin, nigrostriatal cells producing dopamine, etc.) are cultured, put in an appropriate device, and connected with human patients ex vivo, it will supplement or substitute the functions of the damaged organs of the patients.

EXAMPLES

The present invention will specifically be explained in detail with actual examples, but the scope of the invention is not restricted to these samples.

Example 1

① Construction of Transgene

The transgene comprising pMCP's promoter gene and hDAFcDNA is prepared as follows:

From pGL-3 basic vector (Promega), luc gene was clipped out at the NcoI and XbaI sites. Both the ends of the digested vector were truncated with T4 DNA polymerase. Next, hDAFcDNA containing the first intron was clipped out at an AscI site of the upstream locus of initiation codon ATG and at an AccI site of the downstream locus of termination codon TAG, truncated with the T4 DNA polymerase and inserted into the above-described truncated vector. Similarly, an approximately 5.4-kb region corresponding to the promoter gene was clipped out at the EcoRI and FspI sites from the porcine phage genomic library containing PMCP gene (Japanese Patent Application No. 142961/1997), and inserted into the EcoRI and EcoRVsites of the pBluescript vector.

Figure 1:
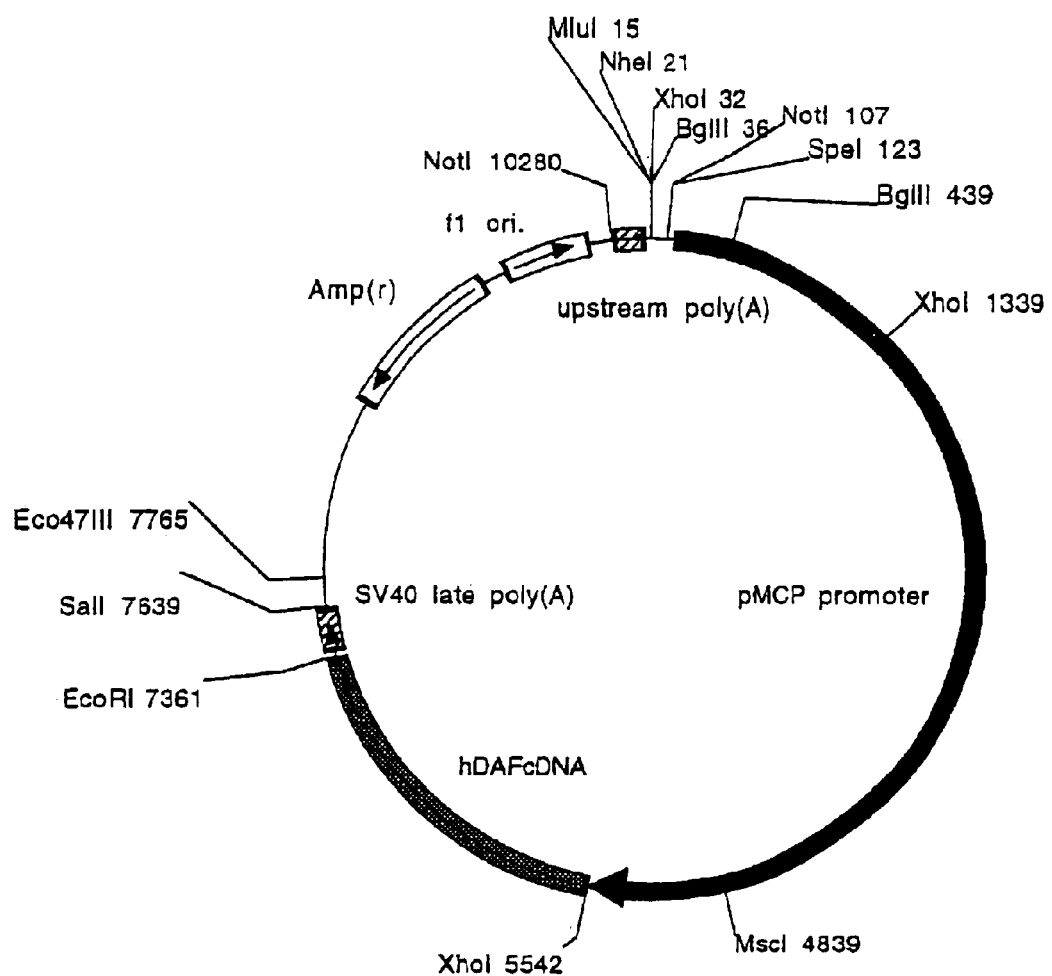
FIG. 1 illustrates the structure of the transgene comprising pMCP promoter (5.4 kb) and hDAFcDNA.

(1) An approximately 5.4-kb promoter region inserted in the pBluescript vector was clipped out at the BstEII and EcoRI sites (the sequence from the second to the 5,392nd bases of Sequence No. 1), truncated with T4 DNA polymerase (the sequence from the second to the 5,397th bases of Sequence No. 1), and then inserted Into an SmaI site at an upstream locus of the above-described hDAFcDNA-inserted vector. The region containing the promoter gene and hDAFcDNA was clipped out at the NotI and Eco47III sites and used as transgene (I) (see FIG. 1).

Figure 2:
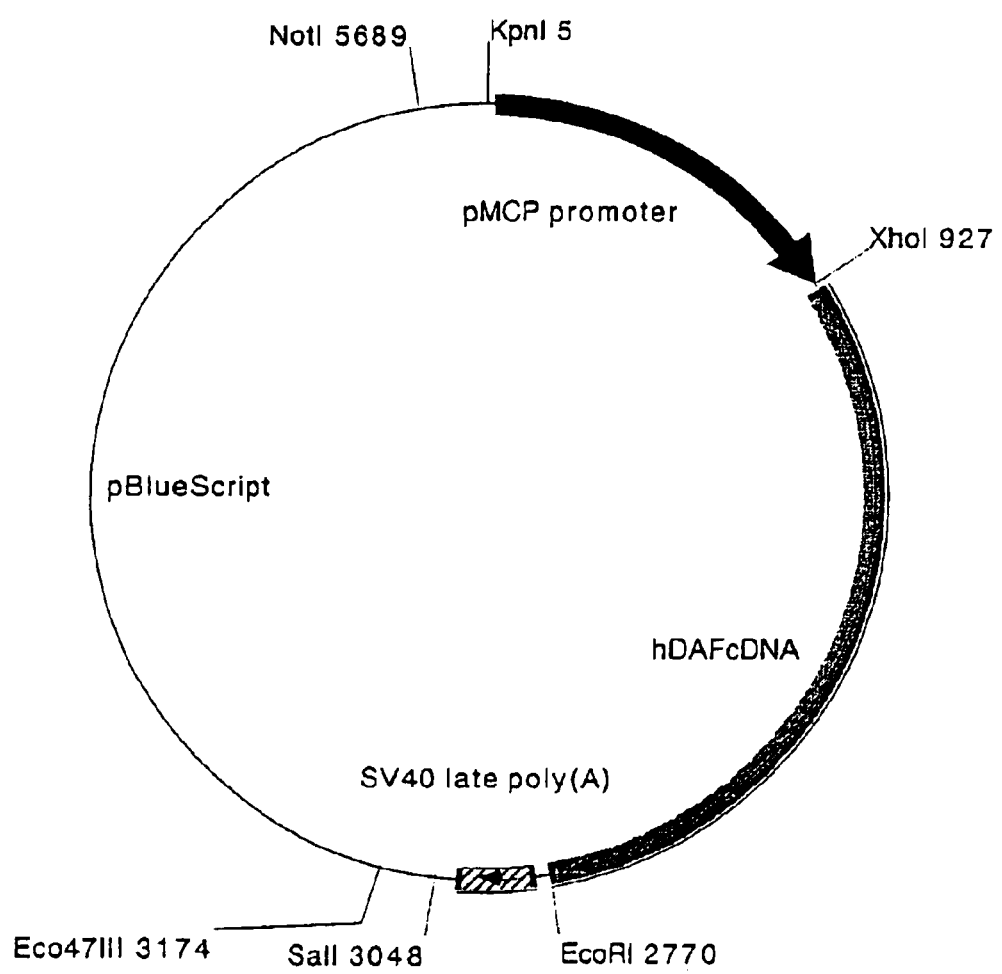
FIG. 2 illustrates the structure of the transgene comprising pMCP promoter (0.9 kb) and hDAFcDNA.

(2) A 1.7-kb promoter region was clipped out at the BstEII and BssH2 sites of upstream loci of the ATG initiation codon of PMCP, truncated with T4 DNA polymerase, and then inserted into the SmaI site of the above-described hDAFcD NA-containing vector. The vector was clipped out at the pBluescript's BstXI and SpeI sites located at further upstream loci of the promoter and linearized. The linearized sequence was digested with a Deletion Kit for Kilo-Sequence (Takara) to obtain a deletion mutant possessing the 0.9-kb promoter gene (the sequence from the 4,498th to the 5,397th bases of Sequence No. 1). The region containing the above-described promoter gene and hDAFcDNA was clipped out at the NotI and Eco47III sites and used as transgene (2) (see FIG. 2).

(3) Transgene (3) comprising hDAF promoter gene and hDAFcDNA was prepared as follows: hDAF promoter gene was prepared by clipping out an approximately3.8-kb region corresponding to the promoter at the HindIII and AscI sites, truncated and inserted to an SmaI site at an upstream locus of the hDAFcDNA-inserted vector. A region containing the above-described promoter gene and hDAFcDNA was clipped out at the NotI and Eco47III sites and used as transgene (3) (see FIG. 3).

Each transgene was dissolved in phosphate-buffered saline (PBS) at 5 µg/ml before used.

② Generation of the Transgenic Mammals (Mice)

The transgenes were introduced into mouse fertilized eggs and the transgenic mice were generated as follows.

CBA or C3H male and C57BL/6 female mice were mated to obtain baby mice, of which female mice (donor mice) were used to supply fertilized eggs. The donor mice were mated with ICR male mice after inducing ovulation (by administration of PMSG and hCG). The fertilized eggs (at the prenucleus phase) were collected. The above-described transgene (1) or (3) was introduced by microinjection into the prenuclei until their swelling was confirmed. The transgene-injected prenucleus-phase eggs were implanted in the uteri of the recipient mice immediately after transduction or in their oviducts after additional incubation for 3 days, and then baby mice were obtained. The recipient mice were made pseudopregnancy by mating them with vasoligated male mice.

③ Generation of Transgenic Mammals (Pigs)

The transgenes were introduced into porcine fertilized eggs and transgenic pigs were generated as follows.

Fertilized eggs were collected from hybrid female pigs (donor pigs) of Landrace, Large White and Duroc. After inducing ovulation of the donor pigs (by administration of either PMSG or FSH, and hCG) and artificial fertilization with semen of male Duroc pig, the fertilized eggs (those at the prenucleus phase) were collected. After centrifugation (for 8 min at 12,000×g) of the prenucleus-phase eggs, transgene (2) was introduced into the prenuclei until swelling was confirmed. The transgene-injected eggs were immediately implanted in the oviducts of the recipient pigs, and then piglets were obtained. The recipient pigs were either pigs whose sexual cycle had been synchronized to those of the donor pigs by the above-described ovulation treatment or those from which the fertilized eggs had been collected.

④ Identification of the Transgenic Mammals

Genomic DNA was extracted from the tails of the youngs obtained from the recipient mammals and subjected to identification and selection of the transgenic mammals by the following two methods:

(1) The dot-blotting method: Genomic DNA (10 µg) from the youngs was placed on a piece of membrane and hybridized with gene comprising a part of biotin-labeled hDAFcDNA. The transgenic mammals were identified by detecting the introduced transgene by an alkaline phosphatase-dependent photon-generating reaction (Sumalight, Sumitomo Metal, Inc.).

(2) PCR method: PCR was carried out (condition; denaturation for 30 sec at 94° C. and annealing for 2 min and 30 sec at 68° C., 30 times) with genomic DNA from the young as a template, 5'-GGCCTTCCCCCAGATGTACCTAATGCC-3' (SEQ ID NO. 2) of hDAFcDNA as a sense primer and 5'-TCCATAATGGTCACGTTCCCCTTG-3' (SEQ ID NO. 3) as an antisense primer. The transgenic mammals were identified by detecting the introduced transgene. The results, shown in FIG. 4 confirmed that some of the youngs obtained from the recipient mammals carried hDAFcDNA in their genome. Lanes 1 and 3 of FIG. 4 show the results with the hDAFcDNA-carrying pig and mouse, respectively. Lanes 2 and 4 of FIG. 4 those of hDAFcDNA-not-carrying littermate pig and mouse, respectively.

⑤ Propagation of the Transgenic Mammals (Mice)

The mice confirmed to be transgenic were mated with ICR mice, and then baby mice carrying the transgene were generated (termed TgF1 mice).

⑥ Confirmation of Expression of the Transgene (Transcription of mRNA) in the Transgenic Mammals (Mice)

By the conventional RT-PCR method, mRNA from various organs of the TgF1 mice was examined for transcription of hDAFcDNA. For comparison, mRNA from those of the transgenic mice generated with transgene (3) comprising hDAF promoter gene and hDAFcDNA and mRNA from those of normal mice (nontransgenic mice) were similarly examined for transcription of hDAFcDNA. The results are shown in FIG. 5. B, H, K, Li, Lu, S and T in FIG. 5 stand for the brain, heart, kidney, liver, lung, spleen and testis, respectively. With the transgenic mice generated by introducing transgene (1) comprising PMCP promoter gene and hDAFcDNA (see FIG. 1), strong signals indicating transcription of mRNA of hDAF were confirmed in all the organs examined (the brain, heart, kidney, liver, lung, spleen and testis) (FIG. 5A). With the transgenic mice obtained by introducing transgene (3) comprising hDAF promoter gene and hDAFcDNA (see FIG. 3), a signal of mRNA of hDAF was observed only in the testis, whereas no or faint signal in other organs (FIG. 5B).

With the nontransgenic mice, no transcription of mRNA of hDAF was observed in any organ (FIG. 5C).

With a cell line of human lymphocyte (K562), transcription of mRNA of hDAF was confirmed (the right end of FIG. 5C).

⑦ Confirmation of Expression of the Transgene in the Transgenic Mammals (Mice) (Confirmation of Expression of hDAF Protein by an Immunohistological Method)

Frozen sections of the TgF1 mouse organs were prepared and treated with biotin-labeled anti-hDAF monoclonal antibodies and then peroxidase-labeled streptavidin. After reaction with a chromogenic substrate (diaminobenzidine; DAB), the sections were microscopically examined for the intensity and the locus of the expressed hDAF protein. The results are shown in Table 1.

With the transgenic mice generated by introducing transgene (1) comprising PMCP promoter gene and hDAFcDNA, it was confirmed that all the organs examined were intensively expressing hDAF. The organs expressing hDAF were artial and ventricular myocardia, and endothelia of medium, small and capillary blood vessels of the heart, glomerulus, uriniferous tubule, and endothelia of medium, small and capillary blood vessels of the kidney, hepatocytes, epithelia of bile ducts, and endothelia of medium, small and capillary blood vessels of the liver, alveolar wall, bronchioles epithelium, and endothelia of medium, small and capillary blood vessels of the lung, epithelia of intestinal mucosa, and endothelia of medium, small and capillary blood vessels of the intestines, exocrine glands, Langerhans islets, epithilia and endothelia of medium, small and capillary blood-vessels of the pancreas, white and red pulp, trabeculare lienis, and endothelia of medium, small and capillary blood vessels of the spleen, cerebral and cerebellar cortex and medulla, and endothelia of medium, small and capillary blood vessels of the brain, seminiferous epithelia, interstitial cells, sperms, and endothelia of medium, small and capillary blood vessels of the testis and peripheral nerves.

With the transgenic mice generated by introducing transgene (3) comprising hDAF promoter gene and hDAFcDNA, the expression of hDAF was confirmed only in the testis, but not in the endothelial cells of the testis.

TABLE 1

| Organ | | Promoter gene used to generate transgenic mouse | | Normal mouse |
|---|---|---|---|---|
| | | pMCP | hDAF | |
| Heart | Artial myocardium | ++ | − | − |
| | Venticuiar myocardium | + | − | − |
| | Endothelia of medium, small and capillary vessels | ++ | − | − |
| Kidney | Glomerulus | ++ | − | − |
| | Uriniferous tubule | − | − | − |
| | Endothelia of medium, small and capillary vessels | ++ | − | − |
| Liver | Hepatocytes | ± | − | − |
| | Epithelia of bile duct | ++ | − | − |
| | Endothelia of medium, small and capillary vessels | ++ | − | − |
| Lung | Alveolar walls | ++ | − | − |
| | Bronchioles epithelium | ++ | − | − |
| | Endothelia of medium, small and capillary vessels | ++ | − | − |
| Intestines | Epithelia of intestinal mucosa | + | − | − |
| | Endothelia of medium, small and capillary vessels | ++ | − | − |

TABLE 1-continued

| | | Promoter gene used to generate transgenic mouse | | Normal mouse |
|---|---|---|---|---|
| | Organ | pMCP | hDAF | |
| Pancreas | Exocrine glands | + | − | − |
| | Langerhans islet | + | − | − |
| | Epithelia pancreatic ducts | + | − | − |
| | Endothelia of medium, small and capillary vessels | ++ | − | − |
| Spleen | White pulp | ± | − | − |
| | Red pulp | ± | − | − |
| | Trabeculare lienis | + | − | − |
| | Endothelia of medium, small and capillary vessels | ++ | − | − |
| Brain | Cerebral cortex | ++ | − | − |
| | Cerebral medulla | ++ | − | − |
| | Cerebellar cortex | + | − | − |
| | Cerebellar medulla | ++ | − | − |
| | Endothelia of medium, small and capillary vessels | ++ | − | − |
| Testis | Seminiferous epithelia | ++ | ± | − |
| | Interstitial cells | + | ± | − |
| | Sperms | ++ | ++ | − |
| | Endothelia of medium, small and capillary vessels | ++ | − | − |
| | Peripheral nerve | +++ | − | − |

⑧ Confirmation of Expression of the Transgene in the Transgenic Mammals (Pigs) (Confirmation of Expression of hDAF Protein by an Immunohistological Method)

Expression of hDAF protein was observed in the pigs which had been identified to be transgenic by the PCR method as described in ④.

Frozen sections were prepared from the tails of the pigs and treated with biotin-labeled anti-hDAF monoclonal antibodies and then peroxidase-labeled streptavidin as described in ⑦. After reaction with the chromogenic substrate (diaminobenzidine; DAB), they were microscopically examined for the intensity and the locus of the expressed hDAF protein.

Expression of hDAF was confirmed in the medium, small and capillary blood vessels of the transgenic pigs generated by introducing transgene (2) comprising the PMCP promoter gene and hDAFcDNA. Besides, expression of hDAF was confirmed also in such organs as the peripheral nerves, skeletal muscle, and stratified squamous epithelia of the skin.

⑨ Confirmation of Expression of the Transgene in the Transgenic Mammal (Pigs) (Confirmation of hDAF-protein Expressing by FACS Analysis)

To examine for hDAF-protein expression, the organs of the transgenic pigs which had been identified to be transgenic by the PCR method as described in ④ and by the immunohistological method as described in ⑦ were subjected to FACS analysis (a fluorescence-activated cell sorter, Becton Dickinson's FACScan) with anti-hDAF monoclonal antibodies.

An erythrocyte fraction was prepared from blood of the transgenic pig, treated with the biotin-labeled monoclonal antibodies and then Phycoprobe PE Streptavidin (Biomeda), and subjected to FACS analysis. The results are shown in FIG. 6(A). Similar analysis as described above was carried out with a nontransgenic littermate pig. The results are shown in FIG. 6(B). The horizontal and vertical axes represent the intensity of fluorescence indicating the amount of hDAF expressed and the cell number, respectively.

As shown in FIG. 6, it was confirmed that the erythrocytes from the transgenic pig identified by PCR and the immunohistological methods expressed huge amounts of hDAF, but that those from the nontransgenic pig did not FIG. 6 shows also that the transgenic pigs of this example simultaneously possessed erythrocytes expressing hDAF and those not expressing hDAF (referred to as mosaic). It has already been shown that the first generation of the transgenic animals (founder) generated by the microinjection method sometimes become mosaic, and that such mosaic may disappear by such conventional methods as mating and breeding.

The results shown in ⑧ and ⑨ confirmed that the transgenic pigs generated by introducing the transgene comprising PMCP promoter and hDAFcDNA expressed hDAF from hDAFcDNA in various organs and tissues including endothelial cells.

⑩ Confirmation of Expression of the Transgene in the Transgenic Mammals (Confirmation of the Function of hDAF Protein)

It was confirmed that the hDAF protein expressed on the transgenic mammals' cells had the essential function of hDAF protein, i.e., suppression of the complement cascade reaction. Confirmation was accomplished by determining hemolysis occurring after treating the transgenic mammal's erythrocytes with human serum. The erythrocytes were subjected to such analyses, since the complement cascade reaction could be identified by observing hemolysis (1) easily due to formation of membrane attack complex, and (2) clearly due to more fragile membrane structure of erythrocytes than other cells (e.g., leukocytes, endothelial cells and the like).

The erythrocyte fractions were prepared from blood specimens taken from the transgenic and nontransgenic mouse tails and those taken from the transgenic and non-transgenic pig ear veins. After diluting the fractions with PBS, a 30-$\mu$l portion of each fraction was placed in a well of 96-well microplates ($1 \times 10^7$ cells/well), to which a 70-$\mu$l portion of complement concentration-adjusted human serum (which had been prepared by blending human normal serum [HNS] and previously inactivated serum (by heating for 30 min at 56° C.) [HIS]) was added dropwise and then allowed to react (for 1.5 h at 37° C.). Optical density of the supernatant of each well was read at 405 nm with a microplate reader (Bio Rad), and the per cent hemolysis caused by the complement cascade reaction was calculated.

The results are shown in FIG. 7, in which figures (a) and (b) respectively show the results with the mouse and porcine erythrocytes. The horizontal and the vertical axes represent the concentration of HNS in human serum and the degree of hemolysis, respectively. Symbols ● and ■ in FIG. 7 show hemolysis of the erythrocytes from the transgenic and the nontransgenic animals, respectively.

Such hemolysis occurs (1) since co-existence of animal erythrocytes and human serum immediately triggers the classical complement pathway due to the presence of the natural antibodies and complement in human serum, and (2) since animal erythrocytes (excluding the transgenic mammals of this invention) cannot inhibit human complement cascade reaction due to the species-specificity of the complement inhibitor.

As shown in FIG. 7, the erythrocytes from nontransgenic animals underwent hemolysis irrespective of the complement concentration in human serum, whereas those from the transgenic mammals inhibited hemolysis. These findings confirmed that the erythrocytes expressing hDAF from the transgenic mammals were resistant to human complement. Although the erythrocyte population of the transgenic pigs of this invention was mosaic, it was resistant to the human complement.

We claim:

1. A transgenic non-human mammal whose genome comprises a nucleotide sequence encoding a human complement inhibitor (DAF/CD55) operably linked to the porcine complement inhibitor (PMCP), consisting essentially of bases 4498 to 5397 of Sequence ID No. 1, said promoter promoting expression of the human complement inhibitor (DAF/CD55), and said mammal expressing the human complement inhibitor in an organ or tissue in amount to prevent hyperacute rejection upon xenotransplantation of said organ or tissue from said transgenic non-human mammal.

2. The transgenic non-human mammal as claimed in claim 1, expressing the human complement inhibitor (DAF/CD55) in endothelial cells.

3. The transgenic non-human mammal as claimed in claim 1, expressing the human complement inhibitor (DAF/CD55) in endothelial cells of organ and tissues of the whole body.

4. The transgenic non-human mammal, as claimed in claim 1, wherein said mammal is a domestic or laboratory mammal.

5. The transgenic non-human mammal as claimed in claim 4, wherein said mammal is a pig or a mouse.

* * * * *

SEQUENCE LISTING

<160> NUMBER OF SEQ ID NOS: 3

<210> SEQ ID NO 1
<211> LENGTH: 5418
<212> TYPE: DNA
<213> ORGANISM: Sus scrofa
<220> FEATURE:
<221> NAME/KEY: misc_feature
<223> OTHER INFORMATION: gamma-FIXII porcine genome phage library
<221> NAME/KEY: misc_feature
<222> LOCATION: (395)..(395)
<223> OTHER INFORMATION: "n' may be a, c, g or t
<221> NAME/KEY: misc_feature
<222> LOCATION: (425)..(425)
<223> OTHER INFORMATION: "n' may be a, c, g or t
<221> NAME/KEY: misc_feature
<222> LOCATION: (766)..(766)
<223> OTHER INFORMATION: "n' may be a, c, g or t
<221> NAME/KEY: misc_feature
<222> LOCATION: (1547)..(1547)
<223> OTHER INFORMATION: "n' may be a, c, g or t
<221> NAME/KEY: misc_feature
<222> LOCATION: (1561)..(1561)
<223> OTHER INFORMATION: "n' may be a, c, g or t
<221> NAME/KEY: misc_feature
<222> LOCATION: (2083)..(2085)
<223> OTHER INFORMATION: "n' may be a, c, g or t
<221> NAME/KEY: misc_feature
<222> LOCATION: (2098)..(2098)
<223> OTHER INFORMATION: "n' may be a, c, g or t
<221> NAME/KEY: misc_feature
<222> LOCATION: (2102)..(2102)
<223> OTHER INFORMATION: "n' may be a, c, g or t
<221> NAME/KEY: misc_feature
<222> LOCATION: (2113)..(2113)
<223> OTHER INFORMATION: "n' may be a, c, g or t
<221> NAME/KEY: misc_feature
<222> LOCATION: (2120)..(2120)
<223> OTHER INFORMATION: "n' may be a, c, g or t
<221> NAME/KEY: misc_feature
<222> LOCATION: (2127)..(2127)
<223> OTHER INFORMATION: "n' may be a, c, g or t
<221> NAME/KEY: misc_feature
<222> LOCATION: (2168)..(2168)
<223> OTHER INFORMATION: "n' may be a, c, g or t
<221> NAME/KEY: misc_feature
<222> LOCATION: (2184)..(2184)
<223> OTHER INFORMATION: "n' may be a, c, g or t
<221> NAME/KEY: misc_feature
<222> LOCATION: (2209)..(2209)
<223> OTHER INFORMATION: "n' may be a, c, g or t
<221> NAME/KEY: misc_feature
<222> LOCATION: (2215)..(2216)
<223> OTHER INFORMATION: "n' may be a, c, g or t
<221> NAME/KEY: misc_feature
<222> LOCATION: (2267)..(2267)
<223> OTHER INFORMATION: "n' may be a, c, g or t
<221> NAME/KEY: misc_feature
<222> LOCATION: (2272)..(2272)
<223> OTHER INFORMATION: "n' may be a, c, g or t
<221> NAME/KEY: misc_feature
<222> LOCATION: (2277)..(2277)
<223> OTHER INFORMATION: "n' may be a, c, g or t
<221> NAME/KEY: misc_feature
<222> LOCATION: (2302)..(2302)
<223> OTHER INFORMATION: "n' may be a, c, g or t
<221> NAME/KEY: misc_feature
<222> LOCATION: (2323)..(2323)
<223> OTHER INFORMATION: "n' may be a, c, g or t
<221> NAME/KEY: misc_feature
<222> LOCATION: (2355)..(2355)
<223> OTHER INFORMATION: "n' may be a, c, g or t
<221> NAME/KEY: misc_feature
<222> LOCATION: (2408)..(2408)
<223> OTHER INFORMATION: "n' may be a, c, g or t
<221> NAME/KEY: misc_feature

```
<222> LOCATION: (2465)..(2465)
<223> OTHER INFORMATION: "n' may be a, c, g or t
<221> NAME/KEY: misc_feature
<222> LOCATION: (2564)..(2564)
<223> OTHER INFORMATION: "n' may be a, c, g or t
<221> NAME/KEY: misc_feature
<222> LOCATION: (2570)..(2570)
<223> OTHER INFORMATION: "n' may be a, c, g or t
<221> NAME/KEY: misc_feature
<222> LOCATION: (2579)..(2579)
<223> OTHER INFORMATION: "n' may be a, c, g or t
<221> NAME/KEY: misc_feature
<222> LOCATION: (2644)..(2644)
<223> OTHER INFORMATION: "n' may be a, c, g or t
<221> NAME/KEY: misc_feature
<222> LOCATION: (2673)..(2673)
<223> OTHER INFORMATION: "n' may be a, c, g or t
<221> NAME/KEY: misc_feature
<222> LOCATION: (2675)..(2675)
<223> OTHER INFORMATION: "n' may be a, c, g or t
<221> NAME/KEY: misc_feature
<222> LOCATION: (3270)..(3270)
<223> OTHER INFORMATION: "n' may be a, c, g or t
<221> NAME/KEY: misc_feature
<222> LOCATION: (3378)..(3378)
<223> OTHER INFORMATION: "n' may be a, c, g or t
<221> NAME/KEY: misc_feature
<222> LOCATION: (3428)..(3428)
<223> OTHER INFORMATION: "n' may be a, c, g or t
<221> NAME/KEY: misc_feature
<222> LOCATION: (3442)..(3442)
<223> OTHER INFORMATION: "n' may be a, c, g or t
<221> NAME/KEY: misc_feature
<222> LOCATION: (3461)..(3461)
<223> OTHER INFORMATION: "n' may be a, c, g or t
<221> NAME/KEY: misc_feature
<222> LOCATION: (3464)..(3464)
<223> OTHER INFORMATION: "n' may be a, c, g or t
<221> NAME/KEY: misc_feature
<222> LOCATION: (3470)..(3470)
<223> OTHER INFORMATION: "n' may be a, c, g or t
<221> NAME/KEY: misc_feature
<222> LOCATION: (3480)..(3480)
<223> OTHER INFORMATION: "n' may be a, c, g or t

<400> SEQUENCE: 1
gaattctgcg tacacggggc cccggtggct ttacatcatc gctacagcga catgggatcc      60
gagccgtgtc tacaacctac acaacaacgc cagatcctta acccaatgca tgaggacagg     120
gctcaaacct gcggcctcat agatgctagt cagattcgtt tctgctgagc acaatggga     180 actcctaatt ctagatcgat ctagaattag gagttcccat tgtggctcag cagaaacgaa     240
tctgactagc atctatgagg ccgcagtttg agccctgtcc tcatgcattg ggttaaggat     300
ctggcgttgt tgtgtaggtt gtagacacgg ctcggatccc atgtcgctgt agcgatgatg     360
taaagccacc ggggccccgt gctacgcaga attcntgcag cccgggggat ccactagttc     420
tagcnagaga gttgaaaatt taaagaacat ttctccccta atctcccaaa atatgggcaa     480
aggacaggta cccgtggcac tggaaaaata caggcaagca acccatgagt acatgaaaag     540
atgctccagg gttcggccta atggaagcct gaacaatgcc tatcacatcg tgggtttctg     600
aagaagtaac ttaaagaaac tagaaattaa atggctttct tagaatgaaa attctctatc     660
acaaggaaaa atgttgtatg ttgttttttcc cataatggag gtcagtgggc gctatgatta     720
acaaatatct gatgcctgtg acttttttaat tgcaagaaat ctgtgnagtt ttttttattat     780 ctatgggaaa tattgcatat attaatgata tcacctaact tgtattattg agcaattctg     840
tccacatctg gcctttcatc tttcatctaa aaagcagggg ctggaccaac tgaccttcag     900
tgccattctt actgctaaca ttctaatttt gtttttattg cctttttgta caaaagtgtg     960
```

-continued

```
agagaagtca ttttaagtct gtgacattaa atgtaatttt ctgtctccag cattataata    1020
agaatcaaag atttaatcta atacaccgat ggaatattgt ttataacgta tttactgttt    1080
caagccttca aaaccaagag aaaacaaaat gagtacctgt tccttctgag aaatgccctt    1140
cttcctgttc agaatccctg tgtataacag gaatgctctc gagttaacag ccaagtaaga    1200
ggcccatcgg ctggcaggtg cccacctagc taggtgcaag cagaggtggc agtgctccca    1260
ggaccaacag cagaaacatg gcttaactat cctgtgttta gcagttctct tacgggtttt    1320
cacaacacct aaaaagcgcc ctgatggggt aaagcctctg ccttcatgct gctgccccgt    1380
ctctgaaaag caggacgtaa atatacaatt taggaggtaa gagggacatc tgccattgtt    1440
ttctttaaca cagtcagcct ctgtttaatg aatcccagcc acctccctcc acctaccatc    1500
attcctaagg tttgcagagg agctgccata gagctcaaaa cacggwntac agacaagcat    1560
nttctccatc cctcctcatc ttctcacagg ccgcttgaca acatctctag gaggggtgg    1620 aggcgccacc agtgtttgag cccctcgttc acgcaaagcc ttgactctgg agttctagtc    1680
ctcgcgggac cttaggaagt tcacggtcaa tactccgccc ttgggctcag acactaagag    1740
gatctccggg taaagagata gacagtagct ccatgcctga tttaggaaaa ctgtccgtac    1800
agacagttgt aattcattcc tttcagagac aaatcctgct ctcttcctag ttcctgaagt    1860
cattaaaatc aaaagctctc agaaacgtcc cagcatttgc taagtccacg ctgggggagg    1920
atgggcagag ccgtgttcag cgcgtttgac agcaacaccc acttatttca ttyagtatcc    1980
ataggcatat atcatgcacc tggtataggc ctctctctca gcactggaga tacagcaaga    2040
aaacgctatt cctgccccat ggagcttgtw maraaaaata gannnaaaaa ccctttanaa    2100
anggaagctr ccngmtgggn cmaagtnaaa attaagtaaa aagaaawccg tgarraaacc    2160
cttcagtnat attaagaaag aaantagctt gatgaaaccc caggtgtana aattnncact    2220
aaaacaatgs tcccaattaa aaccccccmaa ttcatggaat ttactcnagt ancctgnaac    2280
taggraaacc aaattctagc cnatagtttc tcccttctaa atnttctcat gagaaaacaa    2340
yttatttcca aaganatttt ccatgatggg gaaagttttt ttcaactttg ctcaggtata    2400
aactgaaaat acagcattaa agtaaagata gttgcagaga ccaccaaata gatacccgtt    2460
ttcanaaaaa gtgccaacat ggagccagag aacatttccg ttacatcacg cttttacggc    2520
tttgaaaatt aacagagatg ataatccccc mccttgggtt tccnactccn tccctcctna    2580
attttacctc cttttaattgt catcatgtct ggagattata atccaagata ctaagatgtt    2640
tatntcatac atcgcctcca cacagtgtgt ctnanaagct cttgcaagaa tccaaacatt    2700
gtgctggtct gggtagaaaa ggaaattcca tggtttgttg aacccaggaa ctcttcagta    2760
catctccgag gtaaaactgt ttaaatacaa ttaaagttct acagttaaag ggtaccctcc    2820
tccactgttg gtgggaatgt aaactggtac aatcactatg aaaaacagga tggaggtact    2880
tcagaaaatg aagtatagaa ctaccacagg atccagcact ctcactcctg gcacctatc    2940 aggacaaaaa attcgctgca aaagatgcat gcacccatag ctatgttcac tgcagcagca    3000
ttcacaatag ccaagacatg gaaacgacct aaatgtccat caacagctga atgcattaag    3060
aagacgtggt atatacacac aatggaatac tactcaagtc atgaaaaaga acaaaagaat    3120
gccatttgca gcaacatggc atggctgaa ctagagactc atgctaaatg aagtcagtga    3180
gaaagagaaa gacaaatacc acatgatatc acttatatct ggaatctaat atacgacaca    3240
catgaaactt tccacagaaa agaaaacctn catggacttt ggagaacaga cttgtggttt    3300
csccaagggg ggargggggg aagaccgtgg gaggactggg gagctttggg gttaatagat    3360
```

```
gcaaaactat tgcctttnga atggataagc caatgggatc ctgctgtacc agaaccrggg     3420
aactatanct agtcacttgc kntagaacat gatggaggat natntgagan aaagaatatn     3480
tgtgtgtgtk agagagagag agactggctc cactttgctg tatagtagaa aactgacaga     3540
acaccgtaaa ccattaaata aaatccagt aaaaatttaa aataaaaac acacattggt      3600 tccaatgtgt ttaaaagcaa taagttcta taattgcagc agatgcatct gaggtttaca     3660
cggagagctt ccattcctta ccatcctctc attccttaac tctaatgtga tacaggttct     3720
attctcacca ttctatgaac aaaagagcag ctgatttaca ggttggattt ttcaaaaaaa     3780
aaaatttctt taccaggatc ccaaatgtaa caaagggtca atatagaaaa cttaaaaagc     3840
acagccaaag agaaatatac ataagccttt caactattaa ttttgattaa tatccaacga     3900
atctcttttt aagtgtatca atatattatt cattttaata aaagaaattg caagaggcac     3960 ttgcttttc tgcttacaaa tacgtttct caaatcgatt ttttttatat actgtttgca     4020
tagaatttca atccataaag ctacctattg aaaattcctt atatttctgc taaacactta     4080
agggcttata ttttctccaa atttatacat ccttgctcac agttctgacg atgtctttgg     4140
gataaactct aaatggaact agaggtttaa aagttatgtc catttaaaac ttttaacaca     4200 aaaaaggta agtaaaaag taaagtttg gggaggctgc tggtcgcccc cccaacattg     4260
gctgacattt ttattctttg acaacaaata ggaagaaaat gtcaatgtct tttttactg     4320 cttaatactg gtcatgttac ttttctttcc ttttgctaat catacaggct tactcacaac     4380
tctacaaaaa aatcttactc attcctaatg ttccttcatt gagagattgg tttgccggaa     4440
acgttctcac tctcaccaag tcccaacagt cccaactcta acgacggtcg ctgcttccag     4500
aaatacggca cttaaggcac cctcgtcctt acctttttca tgcatgtgta tttcattttc     4560
aataaaacat tgagttgttc caaggccaga ccatagagtt gagccccaac atgctagtgg     4620
cccagtgtga tgtaataatt taccttccca ggggtcctct ccgggggggt acaggcgaga     4680
ctaagtgact ttaagctgtt gggagaacaa tggccaaacc tttcgtgatt ttgaaatcta     4740
tcaggccacg agacacttcg gtagcggacg ctcaaccctg ggaatcccaa ctattgtccc     4800
aaattttgcc tgactcgtgc caaagattga gccagggccc gggtgtccag gcagtctgca     4860
gtgccccagt ccccaccaga gccctgaagg gtgtcgggcc ccacgaaacc gctgcccggg     4920
ctctagggtt tctgttttca ggtcgctgcg ctttattctc taattcagcg ttcccgaaag     4980
agaccatgag gacccgccca gtgtccttta caccttcccg tgtcgggtgg cgacagctgt     5040
ttacgaagaa gagtgcacca cccctttcccg caagccgcag cggttagttc cgcagaagga     5100
ggagccaggg cgtcgggccg cagctgggag agaggcccgg cagcgggcgc gcggagcag     5160 caagggcgtc cctctctcgg ccggagcccc gccccgcccc gccccacgg cccgccttg     5220 cggcccgccc attggctccg ccgggccctg gagtcactcc ctagagccac ttccgcccag     5280 ggcgggcc aggccacgcc cactggcctg accgcgcggg aggctcccgg agaccgtgga     5340
ttcttactcc tgctgtcgga actcgaagag gtctccgcta ggctggtgtc gggttacctg     5400
ctcatcttcc cgaaaatg                                                  5418
```

<210> SEQ ID NO 2
<211> LENGTH: 27
<212> TYPE: DNA
<213> ORGANISM: Artificial Sequence
<220> FEATURE:
<223> OTHER INFORMATION: PCR sense primer -continued

```
<400> SEQUENCE: 2
ggccttcccc cagatgtacc taatgcc                                          27

<210> SEQ ID NO 3
<211> LENGTH: 24
<212> TYPE: DNA
<213> ORGANISM: Artificial Sequence
<220> FEATURE:
<223> OTHER INFORMATION: PCR anti-sense primer

<400> SEQUENCE: 3
tccataatgg tcacgttccc cttg                                             24
```